(12) United States Patent
Kim (10) Patent No.: US 6,528,062 B1
(45) Date of Patent: Mar. 4, 2003

(54) FUNCTIONAL AQUARIUM WATER AND A PREPARATION METHOD THEREOF

(75) Inventor: Jung-Sook Kim, Seoul (KR)

(73) Assignee: Kostarworld Co., LTD, Seoul (KR)

( * ) Notice: Subject to any disclaimer, the term of this patent is extended or adjusted under 35 U.S.C. 154(b) by 0 days.

(21) Appl. No.: 09/883,405

(22) Filed: Jun. 19, 2001

(30) Foreign Application Priority Data

May 12, 2001 (KR) .................................... 2001-0026000

(51) Int. Cl.[7] ........................ A61K 35/84; A61K 35/78; A61K 35/64; A61K 33/24
(52) U.S. Cl. ............... 424/195.16; 424/725; 424/725.1; 424/750; 424/752; 424/769; 424/770; 424/538; 424/771; 424/617
(58) Field of Search ........................... 424/725, 195.16, 424/538, 750, 752, 769, 770, 771, 725.1, 617

(56) References Cited

U.S. PATENT DOCUMENTS 5,753,593 A * 5/1998 Pullen et al.
6,153,208 A * 11/2000 McAtee et al.

FOREIGN PATENT DOCUMENTS

| JP | 9271759 | * | 10/1997 |
| JP | 10287518 | * | 10/1998 |
| KR | 2001020066 | * | 3/2001 |

* cited by examiner

Primary Examiner—Christopher R. Tate
(74) Attorney, Agent, or Firm—Staas & Halsey LLP (57) ABSTRACT

Aquarium water and a preparation method thereof, including a fermented solution of a mixture of extract from leaves of a ginkgo tree, extract from ganoderma, extract from bark of a chestnut tree, extract from acorns, extract from leaves of an evergreen oak tree, extract from bamboo, extract from leaves of a persimmon tree, extract from leaves of a pine tree, water-soluble chitosan powder extracted from crab shells, barley natural stone powder, bamboo salt, potato starch, and distilled water. Fermentation is by adding yeast, and organic germanium, mineral component extracted from yellow soil, and extract from combustion of an oak tree are added. The solution is then fermented again and refined in a liquid state.

6 Claims, 3 Drawing Sheets

[FIG. 1]

Lane 1 : Marker DNA(λ Hind III / EcoR1)
Lane 2 : Marker DNA (100bp ladder)
Lane 3 : Reaction product of the primary PCR
Lane 4 : Reaction product of the secondary PCR

[FIG. 2]

Lane 1: Control group DNA
Lane 2: Nitrosomonas ( the primary PCR : 1.5 kb )
Lane 3: Nitrobacter ( the secondary PCR : 0.49kb )

FIG. 3A
REMOVAL REACTION OF TEA

FIG. 3B
REMOVAL REACTION OF DEA

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: EUB1 primer: forward primer specific for 16s
      rRNA sequence of nitrification bacteria and their relatives

<400> SEQUENCE: 1
gagtttgatc ctggctcag                                                    19

<210> SEQ ID NO 2
<211> LENGTH: 20
<212> TYPE: DNA
<213> ORGANISM: Artificial Sequence
<220> FEATURE:
<223> OTHER INFORMATION: EUB2 primer: reverse primer specific for 16s
      rRNA sequence of nitrification bacteria and their relatives

<400> SEQUENCE: 2
agaaaggagg tgatccagcc                                                   20

<210> SEQ ID NO 3
<211> LENGTH: 20
<212> TYPE: DNA
<213> ORGANISM: Artificial Sequence
<220> FEATURE:
<223> OTHER INFORMATION: FGPS872 primer: forward primer specific for 16S
      rRNA sequence of Nitrobacter bacteria

<400> SEQUENCE: 3
ctaaaactca aaggaattga                                                   20

<210> SEQ ID NO 4
<211> LENGTH: 18
<212> TYPE: DNA
<213> ORGANISM: Artificial Sequence
<220> FEATURE:
<223> OTHER INFORMATION: FGPS1269 primer: reverse primer specific for
      16S rRNA sequence of Nitrobacter bacteria

<400> SEQUENCE: 4 tttttttgaga tttgctag                                                    18

<210> SEQ ID NO 5
<211> LENGTH: 20
<212> TYPE: DNA
<213> ORGANISM: Artificial Sequence
<220> FEATURE:
<223> OTHER INFORMATION: NITROSO4E probe: detecting 16S rRNA of
      Nitrosomonas bacteria

<400> SEQUENCE: 5
cactctagca ttgtagtttc                                                   20

<210> SEQ ID NO 6
<211> LENGTH: 20
<212> TYPE: DNA
<213> ORGANISM: Artificial Sequence

```
-continued

<220> FEATURE:
<223> OTHER INFORMATION: NBAC2 probe: detecting 16S rRNA of Nitrobacter
      bacteria

<400> SEQUENCE: 6
gctccgaaga gaaggtcaca                                                    20
```

FUNCTIONAL AQUARIUM WATER AND A PREPARATION METHOD THEREOF

BACKGROUND OF THE INVENTION

1. Field of the Invention

The present invention is related to aquarium water and a method of its manufacture.

2. Description of the Prior Art

Aquarium water refers to the water kept in an aquarium in order to breed fishes, such as aquarium fishes, etc. The water should be replaced regularly since it degenerates after a fixed amount of storage time. When a new aquarium is installed, there occurs the New Tank Syndrome (N.T.S) in which aquarium fishes die a few days later. The main reason for degeneration of the aquarium water is that discharged and secreted materials of all living bodies, dead aquarium fishes, remaining fodder, moss, air-pollution materials, etc. are accumulated directly as they are or after they are decomposed.

Most substances that flow into the aquarium water are decomposed by the bacteria that live in the water tank naturally. Among them, proteins are decomposed into ammonia ($NH_4+$) by heterotrophic bacteria, where even a small amount of ammonium nitrogen compounds existing in the water tank acts as a fatal poison to aquarium fishes and corals and induces the New Tank Syndrome. Ammonia is decomposed by the nitrification bacteria, of which representative bacteria include nitrosomonas bacteria, decomposing ammonia into nitrous acid ($NO_2-$), and nitrobacter bacteria, decomposing nitrous acid into non-toxic nitrate ($NO_3-$). Therefore, in order to breed aquarium fishes, ammonia should be removed by replacing the aquarium water, or an environment, in which the nitrification bacteria may be multiplied greatly, should be formed.

In the meantime, the moss and algae are multiplied as the phosphorus component is accumulated in the water tank. A proper amount of moss and algae in the water tank may be advantageous since they can be food for aquarium fishes, but an excessive amount of moss and algae multiplied in the water tank may cause aquarium fishes to die since there is not enough oxygen dissolved in the water tank.

Another reason for installing an aquarium in a room is for interior decoration. But the fish-like smell coming from aquarium fishes, mixed with bad odors such as methane ($CH_4$), ammonium ($NH_3$), etc. coming from decomposed components, may make the air in the room undersirably turbid.

After all, it is necessary to replace the aquarium water regularly in order to remove harmful accumulated components, to prevent eutrophication, and to remove smells. However, in many cases, replacement of the aquarium water has been very complicated and burdensome economically, and the water quality has been inferior due to incomplete removal of contamination, even though the aquarium water has been replaced. This eventually has led to development of many methods for prevention of contamination of the aquarium water and for extension of the cycle of replacement.

Accordingly, physical means of improving the situation have been developed including filtering of contamination materials by using filtering agents such as sand, sponge, cotton, activated charcoal, coral thread, etc.; sterilization by inputting ozone; generation of air bubbles in order to increase the amount of oxygen dissolved; etc. However, all of these methods have been for partial effects only, and the aquarium water should be replaced as before.

A method of increasing the amount of oxygen dissolved and seeking to prevent diseases by using drugs such as water-quality improving agents, etc. has been proposed. But this method has been limited in that a separate aquarium for treatment should be used, since most drugs have shown negative effects on living bodies in the aquarium such as bacteria decomposing organic substances, etc. Therefore, the inventions for the biological refinement method that can improve generally the quality of the aquarium water, remove harmful components without negative affects while not disturbing the ecological system in the aquarium, and thus extend significantly the cycle of replacement of the aquarium water eventually are still sought.

SUMMARY OF THE INVENTION

Therefore, the objects of the present invention are to accelerate multiplication and activation of the nitrification bacteria; to increase the amount of oxygen dissolved by preventing eutrophication; to enable easy breeding of aquarium fishes without a need for replacement of the aquarium water by preventing the fish-like smell and removing interior-air-pollution materials; and to form a pleasant in-aquarium and peripheral environment.

In order to achieve the above-described objects, the functional aquarium water of the present invention is prepared by mixing the components having the effects of acceleration of multiplication and activation of the nitrification bacteria; suppression of the fish-like smell; prevention of acidification of pH; prevention of lack of the amount of oxygen dissolved; decomposition ability of harmful components; generation of anions; antimicrobial action; enforcement of the immunization function; maintenance of clearness; and stabilization of hardness at a proper ratio, and refined through the fermentation and maturing processes under the optimum conditions, and the method of its manufacture.

BRIEF DESCRIPTION OF THE DRAWINGS

The foregoing and other objects, aspects, and advantages will be better understood from the following detailed description of a preferred embodiment of the invention with reference to the drawings, in which.

DETAILED DESCRIPTION OF THE EMBODIMENTS

The present invention is related to the functional aquarium water and a preparation method thereof. The functional aquarium water is a mixture of an extract from leaves of a ginkgo tree (*Ginkgo biloba* L.), extract from ganoderma (*Ganoderma japonicum* (Fr.) LLOYD), extract from bark of a chestnut tree (*C. crenata* S. et Z.), extract from acorns, extract from leaves of an evergreen oak tree (*Quercus dentata* THUNB.), extract from bamboo, extract from leaves of a persimmon tree (*Diospyros kaki* THUNB.), extract from leaves of a pine tree (*P. densiflora* S. et Z.), water-soluble chitosan powder extracted from crab shells, barley natural stone powder, bamboo salt, potato starch, and distilled water with yeast added and fermented, and further with the organic germanium, minerals extracted from yellow soil, and extract from combustion of an oak tree (*Quercus acutissima* CARR.) (grass solution) mixed therein and fermented again.

The components and concrete effects of the functional aquarium water of the present invention are described below:

The extracts from the leaves of a ginkgo tree and ganoderma increase the speed of multiplication of the nitrification bacteria and accelerate activation of decomposition. The nitrification bacteria can decompose the substances contaminating the aquarium water, i.e., nitrogen compounds, organic hydrocarbons, etc., as they have an enzyme called ammonia monooxygenase (AMO). Harmful components are accumulated in the aquarium water naturally since the nitrification bacteria are more slowly multiplied than the heterotrophic bacteria that make harmful nitrogen compounds. However, the rates of multiplication and activation of the nitrification bacteria are increased by the above extracts, the decomposition speed of harmful nitrogen compounds is increased, and therefore, the conditions for breeding aquarium fishes are superior, and the interior air is refined as decomposition of volatile organic chemical compounds that are harmful to human bodies, such as benzene, toluene, etc., dissolved into the aquarium water, is accelerated.

The extract from the bark of a chestnut tree decomposes the phosphorus (P) component contained in the aquarium water and suppresses generation of moss.

The extract from acorns decomposes harmful heavy metals such as copper (Cu), phosphorus (P), etc., suppresses generation of green algae, yellow algae, and moss, and prevents decay of the gills of aquarium fishes.

The extracts from bamboo and bamboo salt help cure wounds of aquarium fishes and prevent generation of germs.

The extracts from the leaves of a pine tree, evergreen oak tree, and persimmon tree remove the fish-like smell by generating a large amount of anions and reducing triethylamine (TEA) and diethylamine (DEA) that cause the fish-like smell generated from aquarium fishes. They also prevent decay of the aquarium water by maintaining the amount of oxygen dissolved in the aquarium water at a high level.

The extract from chitosan increases the nutritious components and immunity in case of loss of appetite of aquarium fishes due to stress when they enter into the water tank.

The extracts from barley natural stone powder and organic germanium prevent acidification of the hydrogen iron concentration and maintain the amount of oxygen dissolved to be higher than 9 PPM by fixing the calcium and magnesium ion concentration and maintaining the hydrogen ion concentration with pH 6–7. They also prevent diseases of the gills of aquarium fishes by stabilizing hardness of the aquarium water.

The extract from potato starch prevents the New Tank Syndrome (N.T.S.) by suppressing multiplication of heterotrophic bacteria and accelerating multiplication of the nitrification bacteria.

The extract from yellow soil cures parasitic diseases and inflammation generated on the skin of aquarium fishes, maintains the ratio of oxygen dissolved in the water, and increases clearness of the aquarium water.

The extract from combustion of an oak tree refers to a solution obtained when making charcoal by burning an oak tree. This solution purifies the water by preventing multiplication of germs and decomposing the dead bodies of aquarium fishes perished.

The dried yeast is a product manufactured to contain water of about 8% for easy storage as it is ventilated and dried at a low temperature. It is added during fermentation of the mixture to increase efficiency since it has the same fermentation capability as that of crude yeast.

The method of manufacture of the functional aquarium water of the present invention is described as follows:

Wash the leaves of a ginkgo tree, ganoderma, skin of a chestnut tree, acorns, leaves of an evergreen oak tree, bamboo, leaves of a persimmon tree, and leaves of a pine tree with distilled water, dry them, extract them through continuous reflux below the boiling point, and enrich them at a reduced pressure until the content of solid components is 50–70 weight %. Mix 1–2.5 weight % of the extract from the leaves of a ginkgo tree thus enriched, 1–2.5 weight % of the extract from ganoderma, 1–2.5 weight % of the extract from the bark of a chestnut tree, 1–2.5 weight % of the extract from acorns, 3–4 weight % of the extract from the leaves of an evergreen oak tree, 3–4 weight % of the extract from bamboo, 1–2.5 weight % of the extract from the leaves of a persimmon tree, and 1–2 weight % of the extract from the leaves of a pine tree, and add 0.02–1 weight % of the water-soluble chitosan powder extracted from crab shells, 4–5 weight % of the barley natural stone powder, 0.1–1 weight % of bamboo salt, 0.01–1 weight % of potato starch, and 70–90 weight % of distilled water are mixed, and dried yeast cells are added. The entire solution is then fermented at 30–35° for 28–32 days.

Into 95–98 weight % of the above fermented solution, 0.01–0.1 weight % of the organic germanium, 3–4 weight % of the mineral component extracted from yellow soil, and 1–1.5 weight % of the extract from combustion of an oak tree are mixed, which is then fermented at 20–30° for 85–95 days, and refined in a liquid phase so that no solid components remain.

When using the above refined solution as the aquarium water, 20 weight % of the refined solution and 80 weight % of water are mixed and used at the ratio of 1:4.

The present invention is further described more concretely in terms of several methods of analyses of the functional aquarium water.

Firstly, a method of manufacture of the functional aquarium water of the present invention is described below:

Wash the leaves of a ginkgo tree, ganoderma, skin of a chestnut tree, acorns, leaves of an evergreen oak tree, bamboo, leaves of a persimmon tree, and leaves of a pine tree with distilled water, dry them, and enrich them at a reduced pressure through a continuous reflux extraction below the boiling point so that the content of solid components is 65 weight %. Mix 1.4 weight % of the extract from the leaves of a ginkgo tree, 1.2 weight % of the extract from ganoderma, 1.8 weight % of the extract from the bark of a chestnut tree, 1.62 weight % of the extract from acorns, 3.4 weight % of the extract from the leaves of an evergreen oak tree, 3.2 weight % of the extract from bamboo, 1.4 weight % of the extract from the leaves of a persimmon tree, 1.3 weight % of the extract from the leaves of a pine tree, 0.02 weight % of the water-soluble chitosan powder extracted from crab shells, 4.7 weight % of the barley natural stone powder, 0.2 weight % of bamboo salt, 0.01 weight % of potato starch, and 82.35 weight % of distilled water are mixed, into which dried yeast cells are added at the concentration of 0.1 mg/l. The entire solution is then fermented at 32° for 30 days.

Into 95.38 weight % of the above-described fermented solution, 0.05 weight % of the organic germanium, 3.49 weight % of the mineral component extract from yellow soil, and 1.08 weight % of the extract from combustion of an oak tree are mixed, which is then fermented at 25° for 90 days, and refined in a liquid phase so that no solid components remain.

Secondly, illustrated below is a method of confirmation of the existence of the nitrification bacteria when using the functional aquarium water of the present invention:

The gene detection method is used in order to clarify existence of the nitrification bacteria in the functional aquarium water of the present invention. The aquarium water of the present invention is stored at a water tank. After a fixed amount of time, genome DNA is separated from the bacteria collected by passing the aquarium water through filtering films, and the primary polymerase chain reaction (PCR) is performed by using the following primers, that are consensus primers that may be expanded as they are combined with 16S rRNA of the bacteria having a similar gene map including the nitrification bacteria:

EUB1(forward direction): 5'-GAGTTTGATCCTGGCTCAG-3'

EUB2(reverse direction): 5'-AGAAAGGAGGTGATCCAGCC-3'

Figure 1:
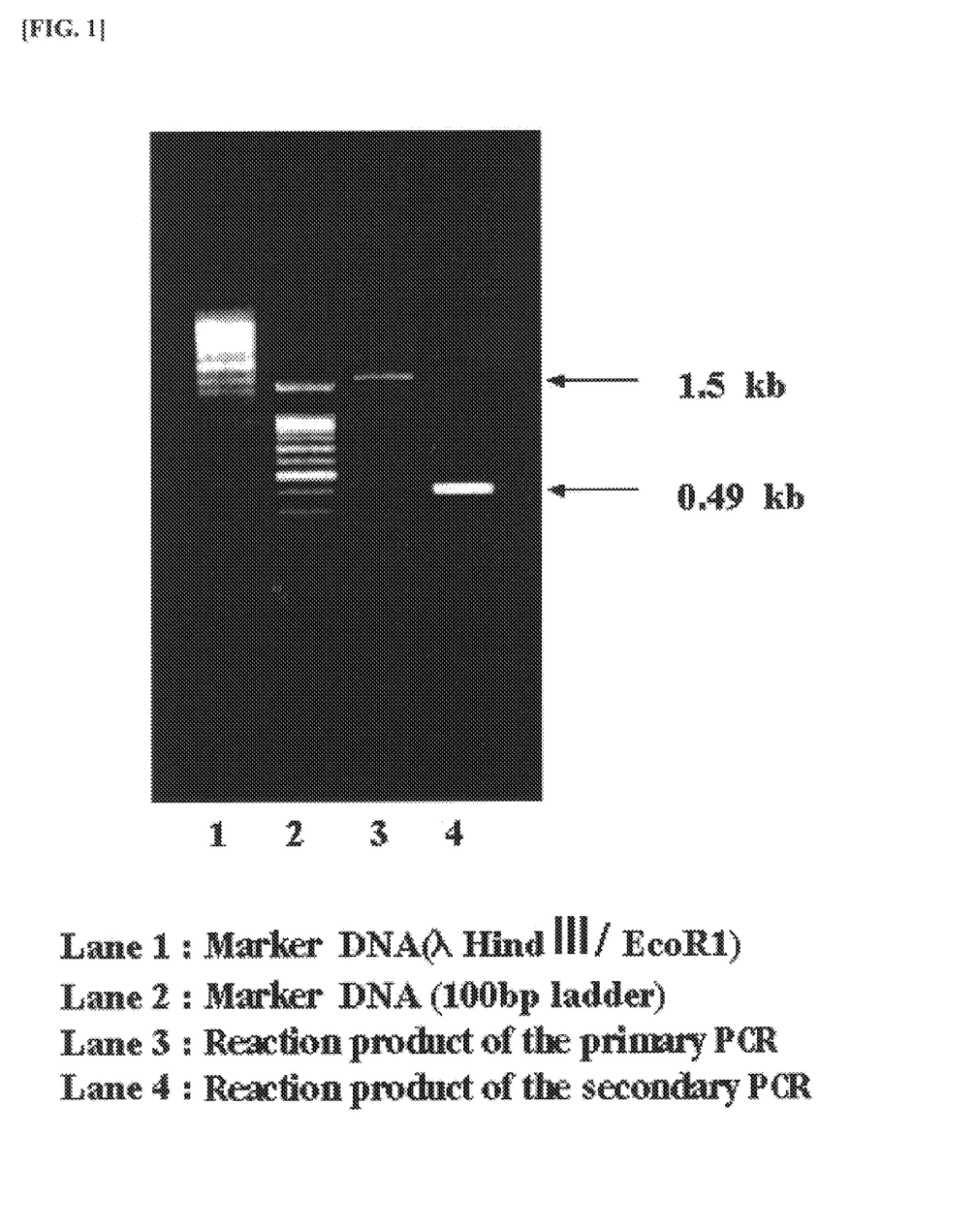
FIG. 1 is a diagram showing the results of PCR that the nitrification bacteria exist in the functional aquarium water of the present invention.

As a result of the primary polymerase chain reaction, the 1.5-Kb band is obtained as shown in FIG. 1. And the secondary polymerase chain reaction is performed by using the following FGPS primers that can expand 16S rRNA gene of nitrobacter selectively and having the above reaction product as the main form:

FGPS872(forward direction): 5'-CTAAAACTCAAAGGAATTGA-3'

FGPS1269(reverse direction): 5'-TTTTTTGAGATTTGCTAG-3'

As a result of the secondary polymerase chain reaction, the 0.49-Kb band is observed as shown in FIG. 1.

In order to re-confirm the above results, each reaction product is analyzed using the Southern Analysis Method. The probe used is combined with 16S rRNA of each of nitrosomonas and nitrobacter complimentarily, and has the following sequence:

Probe NITROSO4E for nitrosomonas: 5-CACTCTAGCATTGTAGTTTC-3'

Probe NBAC2 for nitrobacter: 5'-GCTCCGAAGAGAAGGTCACA-3'

Figure 2:
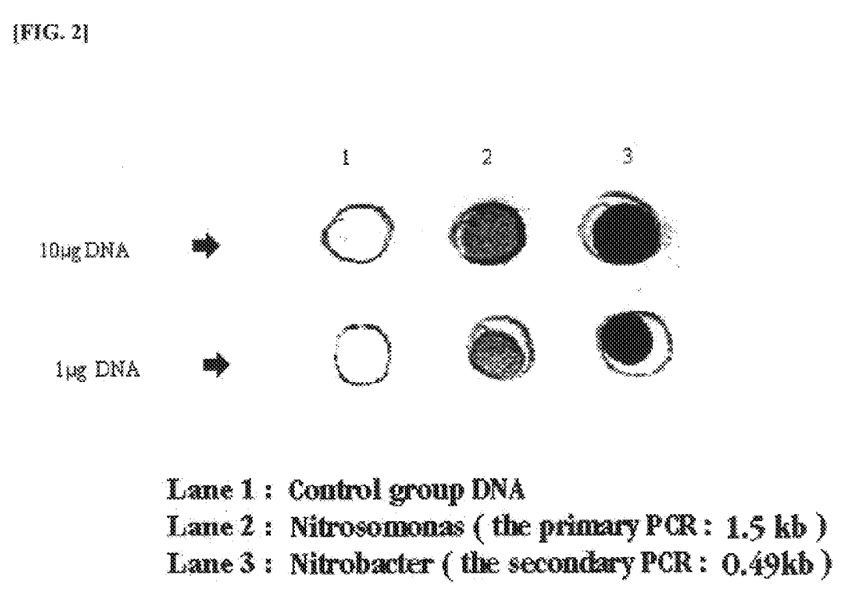
FIG. 2 is a diagram showing the results of Southern Analysis that the nitrification bacteria exist in the functional aquarium water of the present invention.

As a result of the Southern Analysis, it is confirmed that the genes of each bacterium are included in each product of the polymerase chain reaction as shown in FIG. 2.

Through the above results, it is confirmed that there exists the nitrification bacteria in the aquarium in which the functional aquarium water of the present invention is contained.

Thirdly, a method of analysis of the effects of the functional aquarium water of the present invention on multiplication of the cells of nitrification bacteria is suggested as follows:

In order to confirm the effects of the functional aquarium water of the present invention on multiplication of the cells of nitrification bacteria, the same amount of bacteria is vaccinated to the functional aquarium water of the present invention and to ordinary aquarium water, and cultivated for a fixed amount of time. Then the concentration of bacteria is measured and shown in Table 1.

TABLE 1

| Classification | Nitrosomonas | Nitrobacter |
| --- | --- | --- |
| Functional aquarium water | 3.4 * 108 | 6.8 * 107 |
| Ordinary aquarium water | 6.1 * 107 | 1.1 * 107 |

(Unit in cells/Ml)

As shown in Table 1, in the functional aquarium water of the present invention, the 5.7 times higher and 6.3 times higher cell multiplication rates are shown in cases of nitrosomonas and of nitrobacter, respectively, than those in an ordinary aquarium water. It is seen that the multiplication speed of the entire nitrification bacteria is significantly increased from generation of the effects in two steps.

Fourthly, a method of analysis of the effects of the functional aquarium water of the present invention on activation of decomposition of the nitrification bacteria is described below:

In order to confirm the effects of the functional aquarium water of the present invention on activation of decomposition of the nitrification bacteria, each bacterium is washed with the culturing medium, in which the nitrogen compound which is used as its substrate is contained, and is cultured in the functional aquarium water of the present invention and ordinary aquarium water. After a fixed amount of time, the amount of increase of nitrous acid, which is a decomposed product, is measured in case of nitrosomonas since nitrosomonas converts ammonia into nitrous acid; whereas the amount of reduction of nitrous acid, which is a reaction substrate, is measured in case of nitrobacter since nitrobacter decomposes nitrous acid into a nitrate. The results of measurement are shown in Table 2 as follows:

| Classification | Nitrosomonas | Nitrobacter |
| --- | --- | --- |
| Functional aquarium water | +12.1 | −11538 |
| Ordinary aquarium water | +0.6 | −852 |

As shown in Table 2, in the functional aquarium water of the present invention, activation of decomposition is 20.1 times increased in case of nitrosomonas and is 13.5 times increased in case of nitrobacter compared to those in ordinary aquarium water. It is therefore seen from summing up the effects of acceleration of each step that the overall activation is increased by 260 times.

Fifthly, in order to confirm the effects of the functional aquarium water of the present invention on suppression of the fish-like smell, TEA and DEA are mixed into the functional aquarium water of the present invention and ordinary aquarium water, after which the amounts of TEA and DEA remaining in the aquarium water are measured through NMR (Nuclear Magnetic Resonance) at each fixed time interval in order to compare the quantitative amounts of reduction.

Figure 3A:
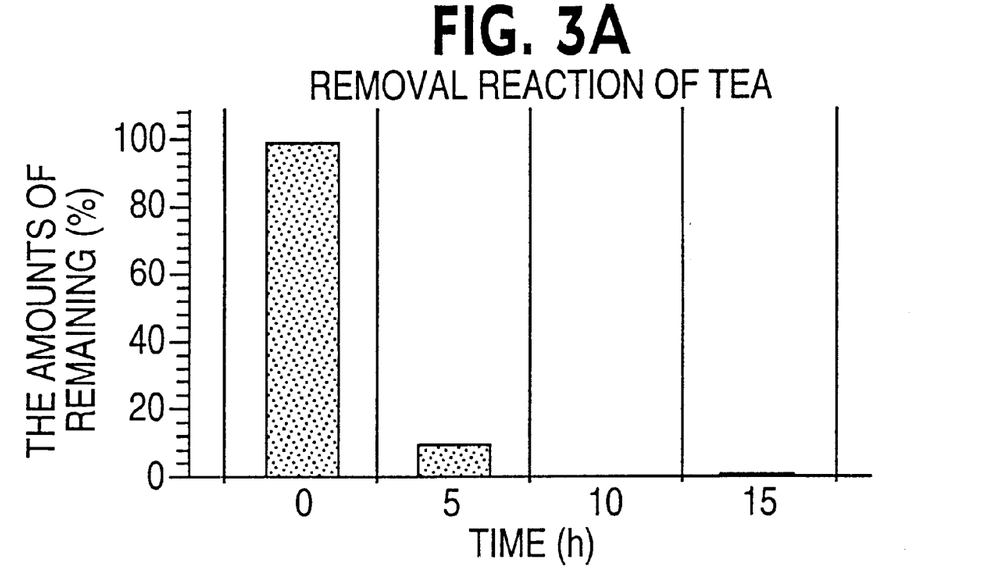
FIG. 3 includes graphs showing the effects of removal of the fish-like smell component from the functional aquarium water of the present invention.
Figure 3B:
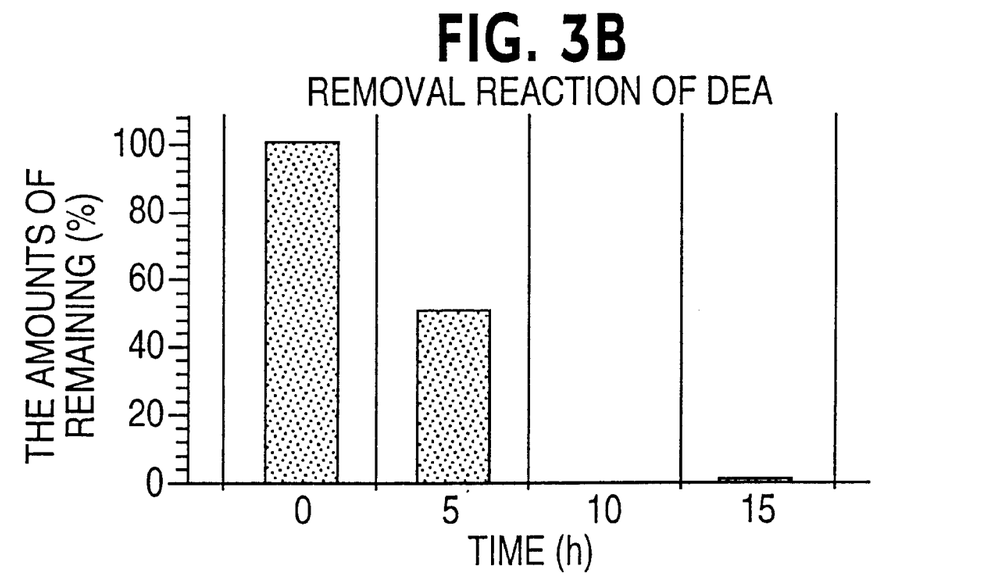

The results of measurement show that TEA and DEA are almost 100% removed from the functional aquarium water of the present invention in about 15 hours as shown in FIG. 3, but that there is almost no change in case of ordinary aquarium water. These results are consistent with the results of comparison through the sense of smell of human beings. It is estimated from computation that the ability of the functional aquarium water of the present invention to remove the fish-like smell is about 104 times greater than that of ordinary aquarium water as the effects of removing the fish-like smell generated per aquarium fish are accumulated for the case of ten aquarium fishes in the water tank.

Sixthly, a method of analysis of the effects of the functional aquarium water of the present invention on purification of the interior air is shown below:

In order to confirm the effects of the functional aquarium water of the present invention on removal of air-pollution materials in a room, the concentrations of volatile organic compounds that are harmful to human bodies are measured in apartments and offices with or without the aquarium, in which the functional aquarium water of the present invention is contained, as shown in Tables 3 and 4.

TABLE 3

Results of measurement of volatile organic compounds in apartments

| Classification | Benzene | Toluene | Ethyl-benzene | m,p-xylene | Styrene |
|---|---|---|---|---|---|
| With an aquarium installed | 1.51 | 47.73 | 4.85 | 3.26 | 3.64 |
| Without an aquarium installed | 1.26 | 10.65 | 2.10 | 1.35 | 1.42 |

(Unit in ppb)

TABLE 4

Results of measurement of volatile organic compounds in offices

| Classification | Benzene | Toluene | Ethyl-benzene | m,p-xylene | Styrene |
|---|---|---|---|---|---|
| With an aquarium installed | 1.61 | 39.70 | Less than detection limit | 1.16 | Less than detection limit |
| Without an aquarium installed | 2.90 | 41.72 | 2.70 | 1.49 | Less than detection limit |

(Unit in ppb)

As shown in Tables 3 and 4, in the apartments and offices with an aquarium, in which the functional aquarium water of the present invention is contained, the concentrations of organic compounds are reduced compared to the case of non-installation of an aquarium. It is seen from this that the functional aquarium water of the present invention has the effects of purifying the air decomposing air-pollution substances existing in a room.

And finally, a method of measurement of the clinical performance of the functional aquarium water of the present invention is suggested as follows:

In order to measure the clinical performance in breeding aquarium fishes in the functional aquarium water of the present invention, 50 aquariums containing the functional aquarium water and 50 aquariums containing ordinary aquarium water were installed to breed aquarium fishes for five years. The survey is performed for 250 people, and the results of general evaluation are shown in Table 5 as follows:

TABLE 5

| Classification | Functional aquarium water | Ordinary aquarium water |
|---|---|---|
| Frequency of replacement of aquarium water | 100 | 10 |
| Maintenance of clearness | 100 | 50 |

TABLE 5-continued

| Classification | Functional aquarium water | Ordinary aquarium water |
|---|---|---|
| Reduction of perishing rate | 80 | 30 |
| Economy | 80 | 10 |
| Healthiness | 80 | 50 |
| Convenience | 100 | 10 |
| Prevention of diseases | 80 | 30 |

※10: very bad,
30: bad,
50: average,
80: good,
100: very good

As shown in Table 5, it is seen that the performance of the functional aquarium water of the present is superior than that of ordinary aquarium water in all aspects. This is consistent with the results of the above experiments. Particularly, it is not necessary to replace the aquarium water for five years in case of an aquarium containing the functional aquarium water of the present invention.

It is expected to have efficient biological purification effects since the functional aquarium water of the present invention accelerates significantly multiplication and activation of the nitrification bacterial that are necessary for maintaining a superior water quality such as nitrosomonas, nitrobacter, etc., and increases the speed of conversion of harmful nitrogen compounds to non-toxic components compared to ordinary aquarium water.

Further, it is expected to have the effects of purifying the in-door air subsequently since the functional aquarium water of the present invention is capable of removing air-pollution materials such as the main component of the fish-like smell coming from aquarium fishes, volatile organic compounds that are harmful to human bodies, etc.

Still further, it is possible to have aesthetic effects through hygienic management of the aquarium and maintenance of clearness at all times since the aquarium water may not be spoiled by thoroughly preventing contamination of the aquarium water and the death rate of aquarium fishes may be lowered significantly by maintaining breeding conditions of aquarium fishes superiorly.

In conclusion, it is possible to obtain the effects of maintaining superior conditions for water quality and the environment without replacing the aquarium water, and of reducing the burden and economical waste of breeding aquarium fishes according to a need for replacement of the aquarium water by using the functional aquarium water of the present invention. Besides the above-described effects, the functional aquarium water of the present invention is applicable to improvement of the contaminated water quality and processing of waste water.

While the invention has been described in terms of preferred embodiments, those skilled in the art will recognize that the invention can be practiced with modification within the spirit and scope of the appended claims.

What is claimed is:

1. Aquarium water which is prepared by the following process:

adding to a fermentation solution, an effective amount of a mixture of components including extract from leaves of a ginkgo tree, extract from ganoderma, extract from bark of a chestnut tree, extract from acorns, extract from the leaves of an evergreen oak tree, extract from bamboo, extract from leaves of a persimmon tree, extract from leaves of a pine tree, a water-soluble chitosan powder extracted from crab shells, barley natural stone powder, bamboo salt, potato starch, and distilled water, whereby the fermentation solution is fermented by admixing yeast thereto, and whereby organic germanium, mineral component extracted from yellow soil, and extract from the combustion of oak trees are then added to the fermentation solution, which is then fermented again and refined to a liquid state.

2. The aquarium water as recited in claim 1, wherein the components are selected to be:

1–2.5 weight % of said extract form the leaves of a ginkgo tree, 1–2.5 weight % of said extract from ganoderma, 1–2.5 weight % of said extract from the bark of a chestnut tree, 1–2.5 weight % of said extract from acorns, 3–4 weight % of said extract from the leaves of an evergreen oak tree, 3–4 weight % of said extract from bamboo, 1–2.5 weight % of said extract from the leaves of a persimmon tree, and 1–2 weight % of said extract from the leaves of a pine tree, 0.02–1 weight % of said water-soluble chitosan powder extracted from crab shells, 4–5 weight % of said barley natural stone powder, 0.1–1 weight % of said bamboo salt, 0.01–1 weight % of said potato starch, and 70–90 weight % of said distilled water, which is enriched at a reduced pressure to have the content of said solid components of 50–70 weight %, and wherein yeast is added to ferment said mixture at 30–35° C. for 28–32 days, and, into 95–98 weight % of the fermented solution is added, 0.01–0.1 weight % of said organic germanium, 34 weight % of said mineral component extracted from yellow soil, and 1–1.5 weight % of said extract from combustion of an oak tree, which is then fermented again at 20–30° C. for 85–95 days and refined in a liquid state.

3. A method of manufacture of aquarium water, comprising the steps of:

adding to a fermented solution, an effective amount of a mixture of components including extract from leaves of a ginkgo tree, extract from ganoderma, extract from bark of a chestnut tree, extract from acorns, extract from leaves of an evergreen oak tree, extract from bamboo, extract from leaves of a persimmon tree, extract from leaves of a pine tree, water-soluble chitosan powder extracted from crab shells, barley natural stone powder, bamboo salt, potato starch, and distilled water, whereby the fermentation solution is fermented by admixing yeast thereto, and whereby organic germanium, mineral component extracted from yellow soil, and extract from the combination of oak trees are then added to the fermentation solution, which is then fermented again and refined to a liquid state.

4. The method as recited in claim 3, wherein the components are selected to be:

1–2.5 weight % of said extract form the leaves of a ginkgo tree, 1–2.5 weight % of said extract from ganoderma, 1–2.5 weight % of said extract from the bark of a chestnut tree, 1–2.5 weight % of said extract from acorns, 3–4 weight % of said extract from the leaves of an evergreen oak tree, 3–4 weight % of said extract from bamboo, 1–2.5 weight % of said extract from the leaves of a persimmon tree, and 1–2 weight % of said extract from the leaves of a pine tree, 0.02–1 weight % of said water-soluble chitosan powder extracted from crab shells, 4–5 weight % of said barley natural stone powder, 0.1–1 weight % of said bamboo salt, 0.01–1 weight % of said potato starch, and 70–90 weight % of said distilled water, which is enriched at a reduced pressure to have the content of said solid components of 50–70 weight %, and wherein yeast is added to ferment said mixture at 30–35° C. for 28–32 days, and into 95–98 weight % of the fermented solution is added 01–0.1 weight % of said organic germanium, 3–4 weight % of said mineral component extracted from yellow soil, and 1–1.5 weight % of said extract from combustion of an oak tree, which is then fermented again at 20–30° C. for 85–95 days and refined in a liquid state.

5. A method for preparing aquarium water, comprising the steps of:

forming aquarium water by adding, to a fermentation solution, an effective amount of a mixture containing components including extract from leaves of a ginkgo tree, extract from ganoderma, extract from bark of a chestnut tree, extract from acorns, extract from leaves of an evergreen oak tree, extract from bamboo, extract from leaves of a persimmon tree, extract from leaves of a pine tree, water-soluble chitosan powder extracted from crab shells, barley natural stone powder, bamboo salt, potato starch, and distilled water, whereby the fermentation solution is fermented by admixing yeast thereto, whereby organic germanium, mineral component extracted from yellow soil, and extract from the combustion of oak trees are then added to the fermentation solution, which is then fermented again and refined to a liquid state, and whereby the aquarium water and water ratio is 1:4.

6. The method as recited in claim 5, wherein the components are selected to be:

1–2.5 weight % of said extract form the leaves of a ginkgo tree, 1–2.5 weight % of said extract from ganoderma, 1–2.5 weight % of said extract from the bark of a chestnut tree, 1–2.5 weight % of said extract from acorns, 3–4 weight % of said extract from the leaves of an evergreen oak tree, 3–4 weight % of said extract from bamboo, 1–2.5 weight % of said extract from the leaves of a persimmon tree, and 1–2 weight % of said extract from the leaves of a pine tree, 0.02–1 weight % of said water-soluble chitosan powder extracted from crab shells, 4–5 weight % of said barley natural stone powder, 0.1–1 weight % of said bamboo salt, 0.01–1 weight % of said potato starch, and 70–90 weight % of said distilled water, which is enriched at a reduced pressure to have the content of said solid components of 50–70 weight %, and wherein yeast is added to ferment said mixture at 30–35° C. for 28–32 days, and into 95–98 weight % of the fermented solution is added 0.01–0.1 weight % of said organic germanium, 3–4 weight % of said mineral component extracted from yellow soil, and 1–1.5 weight % of said extract from combustion of an oak tree, which is then fermented again at 20–30° C. for 85–95 days and refined in a liquid state.

\* \* \* \* \*